(12) United States Patent
Posanski

(10) Patent No.: US 6,503,883 B1
(45) Date of Patent: *Jan. 7, 2003

(54) PHARMACEUTICAL PREPARATIONS FOR THE TARGETED TREATMENT OF CROHN'S DISEASE AND ULCERATIVE COLITIS

(75) Inventor: Ulrich Posanski, Freiburg (DE)

(73) Assignee: Novartis AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/724,526

(22) Filed: Nov. 28, 2000

Related U.S. Application Data

(63) Continuation of application No. 09/407,816, filed on Sep. 28, 1999, now Pat. No. 6,204,243, which is a continuation of application No. 08/980,556, filed on Dec. 1, 1997, now abandoned, which is a continuation of application No. 08/602,849, filed as application No. PCT/EP94/02643 on Aug. 10, 1994, now abandoned.

(30) Foreign Application Priority Data

Sep. 1, 1993 (DE) .......................... 43 29 503

(51) Int. Cl.$^7$ ............................. A61K 38/16
(52) U.S. Cl. ............... 514/8; 514/99; 514/837; 514/867; 514/869; 514/925; 514/964; 424/70.16; 424/451; 424/452; 424/461; 424/463; 424/480; 424/482
(58) Field of Search ................ 514/99, 837, 867, 514/869, 886, 925, 964, 8; 424/70.16, 451, 452, 461, 463, 480, 482

(56) References Cited

U.S. PATENT DOCUMENTS

| 3,959,540 A | 5/1976 | Leiberich et al. ............ 428/35 |
| 5,206,219 A | 4/1993 | Desai ........................... 514/3 |
| 5,286,731 A | 2/1994 | Caufield et al. ............ 514/291 |
| 5,342,625 A | 8/1994 | Hauer et al. ............... 424/455 |
| 5,382,435 A | 1/1995 | Geary et al. ............... 424/489 |
| 5,541,171 A | 7/1996 | Rhodes et al. ............. 514/166 |

FOREIGN PATENT DOCUMENTS

| AU | 10851/83 | 8/1983 |
| BE | 895 724 | 7/1983 |
| EP | 0 148 811 | 7/1985 |
| EP | 0 225 189 | 6/1987 |
| EP | 0 275 796 | 7/1988 |
| EP | 0 533 433 | 3/1993 |
| FR | 2 239 991 | 3/1975 |
| GB | 2166651 | 5/1986 |

OTHER PUBLICATIONS

Derwent Abstracts 90–056185, "Spergualin Preparation Containing Lipids" (1990).
Derwent Abstracts 89/301642/42 (1989).
Derwent Abstracts 90–051911/06 "Unit Dose Delivery System for Hydrophobic . . . " (1990).
R. Bodmeier et al., "Spontaneous Formation of DrugContaining Acrylic Nanoparticles," Journal of Microencapsulation vol. 8, No. 2, pp. 161170 (1991).
E. Allemann et al., "Drug Loaded Nanoparticles—Preparation Methods and Drug Targeting Issues," European Journal of Pharmaceutics and Biopharmaceutics, vol. 39, No. 5, 1993, pp. 173191 (1993).
Handbook of Pharmaceutical Excipients, pp. 362–365 (1975).
Derwent Abstract 90–083371/11, "Enteric solid dosage forms containing active peptide or protein and nonionic surfactant," Feb. 22, 1990.
Derwent Abstracts 95–355166/46 "Adjuvants For Improved Oral Absorption . . . " (1995).

*Primary Examiner*—Frederick Krass
*Assistant Examiner*—Clinton Ostrup
(74) *Attorney, Agent, or Firm*—John D. Thallemer

(57) ABSTRACT

The invention relates to a pharmaceutical preparation, which contains an immunosuppressive active agent in dissolved form in a starch capsule, or hard or soft gelatin capsule which has been coated with one or several polymer films. The invention further relates to a process for the production of the pharmaceutical preparation.

7 Claims, No Drawings

PHARMACEUTICAL PREPARATIONS FOR THE TARGETED TREATMENT OF CROHN'S DISEASE AND ULCERATIVE COLITIS

This application is a continuation of U.S. patent application Ser. No. 09/1407,816, filed Sep. 28, 1999 now U.S. Pat. No. 6,204,243, which is a continuation of U.S. patent application Ser. No. 08/980,556, filed Dec. 1, 1997, now abandoned, which is a continuation of U.S. patent application Ser. No. 08/602,849, filed May 20, 1996, now abandoned, which is a 371 of PCT/EP94/02643, filed Aug. 10, 1994.

The invention relates to a pharmaceutical preparation for the enteral treatment of Crohn's disease and ulcerative colitis, which contains an immunosuppressive active agent, which is administered in the form of a special galenic formulation for targeted local activity in the intestinal area, its use and a process for the production thereof.

The therapies known today for the treatment of Crohn's disease and ulcerative colitis are not very effective. At the end of drug treatment, the patient usually faces surgical intervention. There are numerous preparations for extending and improving the therapeutical possibilities, but until now no preparation has been able to meet the medicinal requirements to a maximum degree.

One possibility of local, enteral therapy of inflammatory intestinal affections was opened up with the development and usage of special mesalazine-containing (5-aminosalicylic acid) preparations, which release the active agent in the distal part of the small intestine and in the large intestine. The preparations concerned are solid forms of administration, which contain the active agent in crystalline form despite its poor solubility.

A new possibility is represented by the use of immunosuppressive active agents which are more effective than the salicylic acid derivatives, but when applied systemically in therapeutically effective dosages have considerable side effects.

The present invention is based on the problem of making available a pharmaceutical preparation for the targeted treatment of Crohn's disease and ulcerative colitis, which contains an immunosuppressive active agent. The activity of the preparation should be targeted at the small and large intestines, and the preparation should ensure local, enteral application of the immunosuppressive active agent at the site of occurrence of the inflammatory disorder.

Surprisingly, an improvement in the rate of effect over the side effects of the immunosuppressive active agent, i.e. a broadening of the therapeutical range, is achieved through the local application of the active agents in the form of a new pharmaceutical preparation, which transports the active agent to the site of occurrence of the inflammatory disorder and allows optimum activity there.

The immunosuppressive active agents from the group of macrolides claimed here are poorly soluble in aqueous media, e.g. in the lumen of the gastrointestinal tract. The dissolution conditions are extremely unfavourable for poorly soluble active agents owing to the small amount of fluid available, especially in the area being envisaged for activity of the preparation, the distal small intestine and the large intestine. As a consequence thereof, the active agent should advantageously be transported to the site of the disorder in an already dissolved form. To this end, ideally, a solution of the active agent is filled into starch capsules, or hard or soft gelatin capsules. The unmodified gelatin capsule or starch capsule does not survive transit through the stomach and the upper small intestine area.

Undesired dissolution of the capsule shell in the area of the stomach or upper small intestine is prevented by coating the external capsule wall with a polymer film. The choice and usage of appropriate polymers, including additional materials such as softeners and pore-forming agents, control the site of dissolution of the capsule and the release of solution containing the active agent.

The object of the invention is a pharmaceutical preparation which contains an immunosuppressive active agent in dissolved form in a starch capsule, or hard or soft gelatin capsule which is coated with one or several polymer films.

A further object of the invention is a process for the production of the preparation according to the invention, which is characterised in that the active agent is dissolved in a solvent which is suitable for encapsulation into starch or gelatin capsules, or in a mixture of several solvents and optionally solubilizers and/or other excipients, the solution is then filled in a manner known per se into starch capsules, or hard or soft gelatin capsules in a measured dose, the capsules are sealed and the capsules are coated with a solution or dispersion of a polymer or polymer mixture and dried, whereby the coating procedure may be repeated once or several times.

The preparation according to the invention is suitable for the local, enteral treatment of Crohn's disease and ulcerative colitis. It contains an immunosuppressive active agent which is poorly soluble in water. The preparation according to the invention contains as active agent rapamycin, tacrolimus, cyclosporin A or combinations of these active agents. The solvents that are appropriate for dissolving the active agent are those that are pharmaceutically acceptable and in which the active agent dissolves.

Examples of these are ethanol, 1,2-propylene glycol, glycerol, polyethylene glycol 300/400, benzyl alcohol, medium-chained triglycerides and vegetable oils.

If required, the usual medicament excipients may be added to the solution of active agent and solvent, for example surface-active agents and agents which affect viscosity. Examples of such excipients are mono-/di-fatty acid glycerides, sorbitan fatty acid esters, polysorbates, Mirj® 52, lecithin, sodium lauryl sulphate, sodium dioctylsulphosuccinate, Cremophor® RH40/EL, aerosil and water-soluble cellulose derivatives.

Mixtures of solvents and the above-mentioned excipients may also be used. The concentration of active agent in the solvent or mixture is adjusted such that it lies between 0.2 and 20% (weight/weight), preferably between 1 and 15% (weight/weight), particularly preferred between 2 and 10% (weight/weight). The solution of the active agent is filled into a conventional starch capsule, or soft or hard gelatin capsule in an amount of 0.05 ml to 2 ml, preferably in an amount of 0.1 to 1.4 ml. The gelatin capsules or starch capsules employed may be those that are normally used in the pharmaceutical field and that are available commercially. If desired, the capsule may be additionally provided with a sealing strip, in order to prevent the solution of active agent from escaping. Production of the soft gelatin capsules is effected for example analogously to the known Scherer processes. The starch capsules are available under the commercial name Capill®.

To enable local enteral application of the immunosuppressive active agents deoxyspergualin, rapamycin, tacrolimus, and cyclosporin A to take place, after swallowing the capsule, there must be passage of the intact capsule through the stomach and the upper small intestine region. To this end, the soft or hard gelatin capsule is coated with one or several polymer films, whereby the targeted capsule dissolution and release of active agent is achieved through the film composition. Two principles or a combination of these principles may be offered for this purpose:
1. Premature dissolution of the capsule is prevented by coating the capsule with a polymer film containing acid groups, whereby the type of acid and the number of acid groups control dissolution of the film in dependence of the pH value of the surroundings.
2. Dissolution of the capsule is controlled by diffusion mechanisms, whereby the polymer film is insoluble in water and the diffusion operations are influenced by additional substances such as water-soluble pore forming agents and softeners.

Within the sense of this invention, especially suitable polymers for principle 1 are:

Cellulose-acetate trimellitate, -acetate succinate, -acetate phthalate, hydroxypropyl methylcellulose phthalate, -acetate succinate, carboxymethylethyl cellulose (Trade name e.g. Duodcell®), polyvinyl acetate phthalate (commercial products, e.g. Coateric®, Opadry Enteric®), copolymerisates of vinyl acetate and crotonic acid (commercial product, e.g. Coating CE 5142®), polymethacrylates, e.g. copolymerisates of methacrylic acid and methyl-methacrylate, copolymerisates of methacrylic acid and ethyl acrylate (commercial products are e.g. Eudragit® L/L30D). Mixtures of these polymers may also be used.

Suitable polymers for principle 2 are:

Methylcellulose (Trade name e.g. Methocel), ethylcellulose (commercial product e.g. Ethocel®, Aquacoat® ECD30), cellulose acetate, cellulose acetate propionate, cellulose acetate butyrate, polyvinyl derivatives, e.g. polyvinyl alcohol, polyvinyl acetate, vinyl acetate/vinyl pyrrolidone copolymers (commercial products are e.g. PVP-VA types of GAF), copolymerisates of methacrylic acid and ethyl acrylate (commercial products are e.g. Eudragit® RL/RS/NE30D/RL30D/RS30D), copolymerisates of polymethyl vinyl ether and malonic acid anhydride, copolymerisates of polymethyl vinyl ether and malonic acid or the ethyl-, isopropyl-, n-butylesters thereof (commercial products are e.g. the Gantrez® polymers of the series ES/AN/S), or mixtures of these polymers.

Moreover, for both principles, the thickness of the polymer film on the capsule surface is significant for the progress of capsule dissolution and the release of active agent. The required film thickness may differ individually for each polymer. In addition, it depends on other excipients, e.g. softeners, the solvent or dispersing agent used during the film-coating process, the film application technique, and the capsule shape. In practice, the amounts applied lie between 1 mg/cm$^2$ and 100 mg dry film substance/cm$^2$ capsule surface. The proportion by weight of the dried film coating on the whole medicinal substance is normally less than 10% (by weight).

If both principles are used in combination and the polymers are applied separately, then one film serves as an external film corresponding to principle 1. This external film must have a dissolution time of more than 2 hours in the gastric juices.

The properties of the polymer films may be further influenced by additions of pore-forming agents and softeners. Suitable pore-forming agents to form open pores and thus to increase the diffusion rate through the polymer coating are water-soluble substances, e.g. lactose, saccharose, sorbitol, mannitol, glycerol, polyethylene glycol consisting of less than 6000 ethylene oxide units, 1,2-propylene glycol, hydroxypropyl cellulose, hydroxypropyl methylcellulose, methylcellulose, as well as mixtures thereof. The proportion by weight of the pore-forming agents on the dried film coating is less than 20% (weight/weight).

Suitable softeners are the alkyl esters of citric acid, tartaric acid and 1,8-octanedicarboxylic acid, e.g. triethyl citrate, tributyl citrate, acetyl triethyl citrate, dibutyl tartrate, diethyl sebacate, or resp. esters of phthalic acid, e.g. dimethyl phthalate, diethyl phthalate, dioctyl phthalate, or resp. glycerol esters, e.g. castor oil, sesame oil, acetylated fatty acid glycerides, glycerol triacetate, glycerol diacetate, or resp. higher alcohols, e.g. glycerol, 1,2-propylene glycol, or resp. polyethers, e.g. polyethylene glycols and polyoxyethylene-polypropylene block copolymers, or resp. wetting agents, e.g. PEG-400 stearate, sorbitan monooleate, PEG-sorbitan mono-oleate.

For application, the polymer or a mixture of polymers is dissolved or dispersed in an organic solvent or in a solvent mixture. Suitable solvents are for example ethanol, isopropanol, n-propanol, acetone, ethyl acetate, methyl ethyl ketone, methanol, methylene chloride, tert.-butanol, propylene glycol monomethyl ether and water.

Solvent mixtures or mixtures of these solvents with water may also be used. For better processing of the film coatings, the usual excipients may be added to them, for example colloidal silicon dioxide, talcum and magnesium stearate. In order to apply and dry the polymer film, all known processes for applying films to tablet or pellets are suitable, e.g. dip-sword, immersion tube, coating, fluidised bed, Wurster column, Accela-Cota, Hi-Coater, Driacoater or ball-coater processes.

The person skilled in the art may determine the properties of the polymer films by means of simple preliminary tests. It is especially important here that, after swallowing the preparation, the intact capsule is allowed to pass through the stomach and the upper small intestine.

For example, the coated capsules undergo a test of the release of active agent according to USP in a "dissolution rate" testing apparatus having a small rotating basket. To this end, the capsules are first of all exposed to artificial gastric juice for two hours. Afterwards, the medium is changed over to artificial intestinal juice pH 6.8. After a further four hours, it is adjusted to artificial intestinal juice pH 7.2. During the whole duration of the test, the concentration of active agent in the medium is determined continuously e.g. using a suitable HPLC method. During the testing periods, the active agent should not be detectable in the artificial gastric juice nor in the artificial intestinal juice pH 6.8, since otherwise the intact capsule would not be allowed to pass to the site of action.

The following examples illustrate the invention without restricting it.

EXAMPLE 1

The following solution of active agent is filled into oval soft gelatin capsules of size 5 minims:

Amounts in mg/capsule content after production:

| | |
|---|---|
| cyclosporin A | 25.0 |
| ethanol 96% | 25.0 |
| polyoxyethylene-(40)-hydrogenated castor oil | 87.5 |
| neutral oil | 50.0 |
| di/tri/tetraglycerol fatty acid ester | 62.5 |

Two polymer films are subsequently applied to the dried soft gelatin capsules. To this end, 250,000 soft gelatin capsules are filled into an Accela-Cota (AC48). 15.0 kg of the first polymer solution are sprayed on, and the solvent is continuously removed during the process. The temperature of the air supply for drying the capsules is 35° C.

The first polymer solution consists of (amounts in % by weight):

| | |
|---|---|
| ethyl cellulose | 5.0 |
| triacetine | 1.0 |
| polyethylene glycol 1500 | 0.6 |
| ethanol 96% | 93.4 |

The second polymer solution consists of (amounts in % by weight):

| | |
|---|---|
| hydroxypropyl methylcellulose phthalate (HP-55) | 8.0 |
| dist. acetylated glycerides | 0.8 |
| acetone | 46.0 |
| ethanol 95% | 45.2 |

13.5 kg of the second solution are applied in the same apparatus. The air supply temperature is lowered to 30° C. After ending the film application, the temperature is raised to 40° C. to remove residual solvents.

EXAMPLE 2

The following solution of tacrolimus is filled into soft gelatin capsules of size 8 minims:

Amount of capsule content in mg per capsule after production:

| | |
|---|---|
| tacrolimus | 10.0 |
| polysorbate 80 | 270.0 |
| neutral oil | 135.0 |
| sorbitan monolaurate | 45.0 |

A cellulose acetate film is applied to the dried capsules. To this end, 150,000 capsules are filled into a driacoater (DR 1200) having a solvent recovery system. The air supply temperature during film coating is set at 30° C. The sprayed polymer solution has the following composition:

| | |
|---|---|
| cellulose acetate | 5.0 |
| polyethylene glycol 4000 | 0.3 |
| acetone | 80.0 |
| water | 14.7 |

EXAMPLE 3

A solution containing the active agent rapamycin is filled into hard gelatin capsules of size "1". The amounts correspond to the capsule content in mg.

| | |
|---|---|
| rapamycin | 5.0 |
| polysorbate 60 | 230.0 |
| polyethylene glycol 400 | 190.0 |
| glycerol | 5.0 |

-continued

| | |
|---|---|
| 1,2-propylene glycol | 20.0 |
| total content | 450.0 |

In addition to this, there is the weight of the empty capsule at 77 mg. Three polymer solutions are applied in succession to these filled hard gelatin capsules (amounts respectively given in % by weight).

The composition of the first solution:

| | |
|---|---|
| hydroxypropyl cellulose | 7.5 |
| polyethylene glycol 1500 | 0.5 |
| ethanol 96% | 92.0 |

This polymer film is applied to seal the capsules and assists the remaining processing stages (undercoat).

The composition of the second solution:

| | |
|---|---|
| Eudragit RS 30D | 27.0 |
| Eudragit RL 30D | 6.0 |
| triethyl citrate | 2.0 |
| talcum | 2.5 |
| water | 62.5 |

The composition of the third solution:

| | |
|---|---|
| hydroxypropyl methylcellulose acetate succinate | 10.0 |
| triethyl citrate | 3.0 |
| talcum | 3.0 |
| water | 84.0 |

Film coating is effected in a fluidised bed apparatus. The air supply temperature during film application is 48° C. The spray rate and air diffusion are set such that the outgoing air temperature remains at 21° C.

What is claimed is:

1. A pharmaceutical composition comprising
   (a) a solvent in which rapamycin is soluble;
   (b) rapamycin dissolved in the solvent forming a solution of rapamycin;
   (c) a capsule selected from the group consisting of a starch capsule, hard gelatin capsule, and soft gelatin capsule, wherein the capsule encapsulates the solution of rapamycin;

wherein said capsule is coated with at least one polymer composition containing at least one pore-forming agent in an amount effective to increase the diffusion rate through the polymer coating.

2. The pharmaceutical composition according to claim 1 wherein the polymer is selected from the group consisting of a cellulose derivative, methacrylic acid derivative, polyvinyl derivative, and combinations thereof.

3. The pharmaceutical composition according to claim 1 wherein the polymer is selected from the group consisting of methylcellulose, ethylcellulose, cellulose acetate, cellulose acetate butyrate, cellulose acetate phthalate, cellulose acetate trimellitate, cellulose acetate propionate, hydroxypropyl methylcellulose, hydroxypropyl cellulose, hydroxypropyl methylcellulose phthalate, hydroxypropyl methylcellulose acetate succinate, polyvinyl alcohol, polyvinyl acetate, polyvinyl acetate phthalate, methylacrylic acid/methyl-methacrylate copolymers, methacrylic acid/ethyl-acrylate copolymers, polymethyl vinyl ether/malonic acid anhydride copolymers, polymethyl vinyl ether/malonic acid-ethyl, -isopropyl, -n-butylester copolymers, and combinations thereof.

4. The pharmaceutical composition according to claim 1 wherein the pore-forming agent is selected from the group consisting of lactose, saccharose, sorbitol, mannitol, glycerol, polyethylene glycol having less than 6000 ethylene oxide units, 1,2-propylene glycol, hydroxypropyl cellulose, methylcellulose, and mixtures thereof.

5. The pharmaceutical composition according to claim 1 wherein the concentration (w/w) of rapamycin in the encapsulated solution is 0.2 to 20%.

6. The pharmaceutical composition according to claim 1 wherein the rapamycin is released from the capsule in the small and/or large intestinal area of a human.

7. The pharmaceutical composition according to claim 1 for the treatment of Crohn's disease and ulcerative colitis.

* * * * *